United States Patent [19]

Sullivan et al.

[11] Patent Number: 5,243,971
[45] Date of Patent: Sep. 14, 1993

[54] NASAL MASK FOR CPAP HAVING BALLOONING/MOULDING SEAL WITH WEARER'S NOSE AND FACIAL CONTOURS

[75] Inventors: Colin E. Sullivan, Birchgrove; Jakob W. Bruderer, Kingsford, both of Australia

[73] Assignee: The University of Sydney, Sydney, Australia

[21] Appl. No.: 912,129

[22] Filed: Jul. 9, 1992

Related U.S. Application Data

[63] Continuation of Ser. No. 702,616, May 17, 1991, abandoned.

[30] Foreign Application Priority Data

May 21, 1990 [AU] Australia .................. PK0228

[51] Int. Cl.$^5$ ............ A62B 18/02; A62B 18/08; A61M 15/08
[52] U.S. Cl. .................. 128/205.25; 128/204.18; 128/206.24; 128/207.13; 128/207.18
[58] Field of Search ............. 128/203.22, 204.11, 128/204.12, 204.18, 205.25, 206.18, 206.26, 206.28, 207.13, 207.18, 206.24

[56] References Cited

U.S. PATENT DOCUMENTS

| | | | |
|---|---|---|---|
| 844,097 | 2/1907 | Caldwell | 128/203.22 |
| 1,048,491 | 12/1912 | Butcher | 128/203.22 |
| 1,206,045 | 11/1916 | Smith | 128/206.24 |
| 1,635,275 | 7/1927 | Johnson | 128/207.13 |
| 1,653,572 | 12/1927 | Jackson | 128/206.24 |
| 2,241,535 | 5/1941 | Boothly et al. | 128/207.13 |
| 2,415,846 | 2/1947 | Randall | 128/206.24 |
| 2,578,621 | 12/1951 | Yant | 128/206.24 |
| 2,765,788 | 10/1956 | Raiche | 128/206.28 |
| 2,931,356 | 4/1960 | Schwarz | 128/206.24 |
| 3,330,273 | 7/1967 | Bennett | 128/206.26 |
| 3,330,274 | 7/1967 | Bennett | 128/206.26 |
| 3,725,953 | 4/1973 | Johnson et al. | 128/206.26 |
| 4,559,940 | 12/1985 | McGinnis | 128/206.26 |
| 4,655,213 | 4/1987 | Rapoport et al. | 128/205.25 |
| 4,782,832 | 11/1988 | Trimble et al. | 128/204.18 |
| 4,919,128 | 4/1990 | Kopala et al. | 128/205.25 |
| 4,944,310 | 7/1990 | Sullivan | 128/205.25 |

FOREIGN PATENT DOCUMENTS

| | | |
|---|---|---|
| 207751 | 4/1907 | Fed. Rep. of Germany ............ 128/206.24 |
| 1104122 | 4/1961 | Fed. Rep. of Germany . |
| 3707952 | 9/1988 | Fed. Rep. of Germany . |
| 492723 | 9/1938 | United Kingdom ........ 128/207.13 |
| 697762 | 9/1953 | United Kingdom . |
| 775911 | 5/1957 | United Kingdom ........ 128/206.26 |
| 848215 | 9/1960 | United Kingdom . |
| 1360632 | 7/1974 | United Kingdom ........ 128/206.24 |

OTHER PUBLICATIONS

Patterson & Gormezano, "A Mask for rabbit stereotaxic . . . ", *Behavior Research Methods & Instrumentation*, 1978, vol. 10(1), 41–42.
European Search Report for European Patent Application 91 30 4512.

*Primary Examiner*—Edgar S. Burr
*Assistant Examiner*—Kimberly L. Asher
*Attorney, Agent, or Firm*—Merchant, Gould, Smith, Edell, Welter & Schmidt

[57] ABSTRACT

A nasal mask which is suitable for use in a continuous positive airway pressure system. The mask has a face contacting portion mounted to a shell which is sized and shaped to overfit the nose region of an intended wearer, and the face contacting portion is in the form of a distendable membrane which is moulded from an elastic plastics material. The distendable membrane and the shell together define a chamber, and pressurised gas admitted to the chamber causes the membrane to distend outwardly from the shell. When placed in contact with the face of the wearer, the distendable membrane is caused to overlay the covered facial regions and, under the influence of the pressurised gas, to conform three-dimensionally with the contours of the overlayed regions. An orifice is formed within the membrane and is shaped and positioned to admit gas from the chamber to the nasal passages of the wearer.

19 Claims, 5 Drawing Sheets

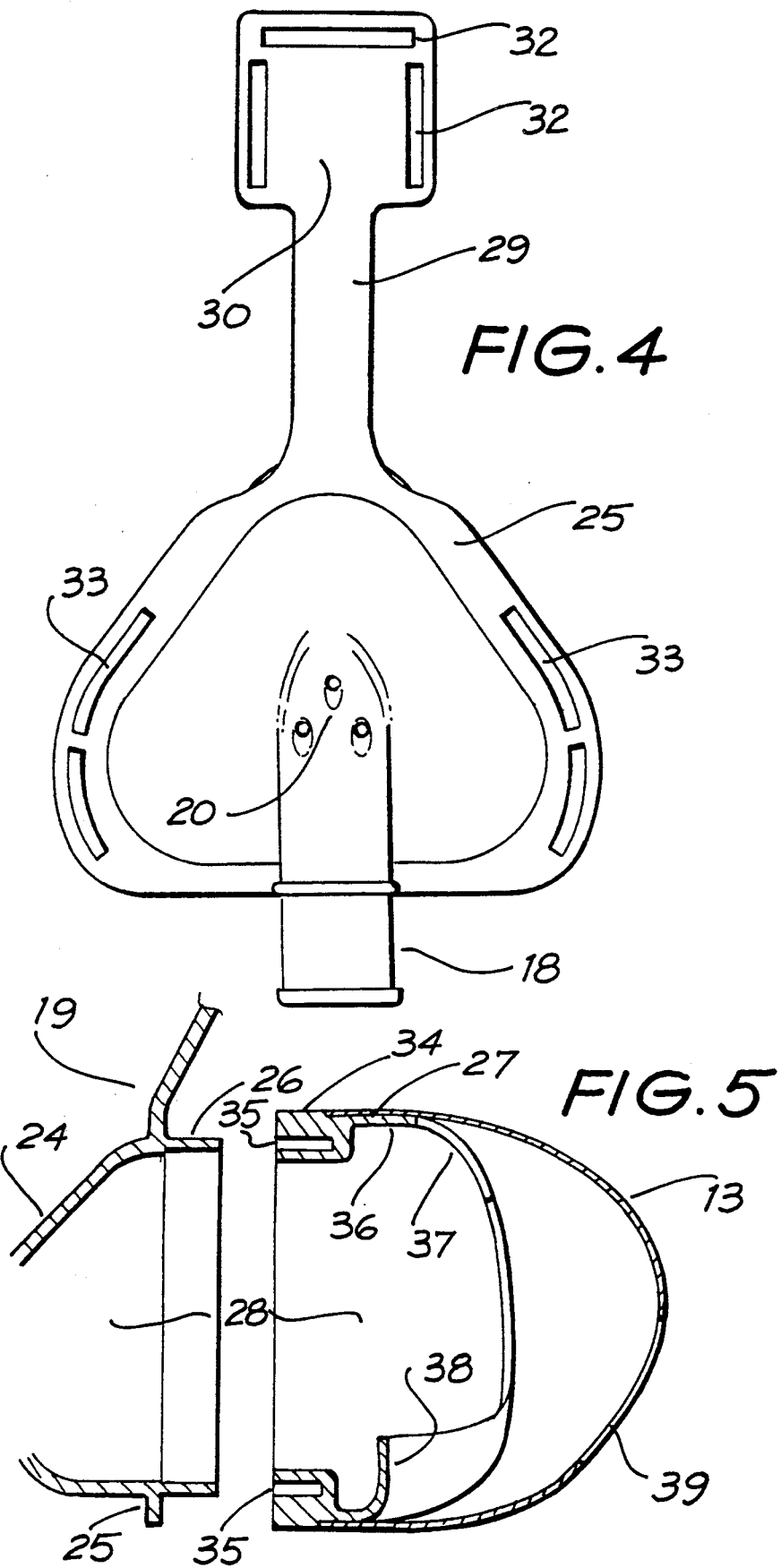

NASAL MASK FOR CPAP HAVING BALLOONING/MOULDING SEAL WITH WEARER'S NOSE AND FACIAL CONTOURS

This is a continuation of copending application(s) Ser. No. 07/702,616 filed on May 17, 1991, now abandoned.

FIELD OF THE INVENTION

This invention relates to a nasal mask and, in particular, to a mask that has the facility to conform to the facial contours of a wearer.

BACKGROUND OF THE INVENTION

Nasal masks currently are employed for various purposes, including for the delivery of oxygen to persons who suffer lung disease or who are exposed to rarefied atmospheres, for administering anaesthesic gases and for delivering pressurised air to persons who suffer from such disorders as sleep apnea. The masks usually are moulded from a relatively soft, resilient plastics material and they are shaped during manufacture to match the facial contours of an average intended wearer. However, a problem with the known types of masks is that, because individuals vary so much from the average, the masks must be forced against their inherent resiliency to deform and so adapt to the shapes of the users in order to avoid gas leakage. This requires that the masks be secured firmly by retaining straps or harnesses in order to prevent air leakage and, depending on the degree of deformation required in any given case, may produce discomfort, irritation or even ulceration of the upper lip and/or the nasal bridge where there is little cushioning from subcutaneous tissue. Thus, the retaining force normally is distributed over a relatively small sealing area defined by the peripheral edge of the mask and this causes a relatively high localised pressure to be exerted on the face of the wearer. Also, because the sealing area is relatively small in the currently employed masks, minor dislocation of a mask may produce a significant leakage path for gas.

Attempts have been made to overcome the above difficulties by shaping perimeter edges of some masks in such a manner that the edges tend to move with a rolling action when a mask is pushed into contact with a wearer's face. This shaping permits differential movement around the perimeter of a mask and facilitates adaptation of the mask to the facial contours of the wearer.

Also, U.S. Pat. No. 4,971,051 discloses a mask which has been developed in an attempt to provide both comfortable and conformable perimeter sealing, the mask having a flexible pneumatic cushion formed around its perimeter and/or being provided with a so-called flap ring which is formed as an adjunct to the mask. The flap ring comprises a flexible membrane which is affixed to the perimeter of the mask and it acts in the manner of a flap valve when blown against a wearer's face by air delivered to the interior of the mask.

A problem which is inherent in a mask of the type disclosed in U.S. Pat. No. 4,971,051 is that the flap ring is constrained by its attachment to the perimeter seal of the mask and its freedom to adapt to facial contours is limited. Moreover, again because the flap ring is attached to the perimeter seal of the mask, any movement of the perimeter seal may cause movement of the flap ring relative to the wearer's face and thereby open a path through which gas may leak. Similarly, movement of the flap ring may cause stresses to be imposed on the perimeter seal, so that a path may be created through which gas may leak.

SUMMARY OF THE INVENTION

In contrast with the prior art masks, the present invention provides a nasal mask which comprises:

(a) a face contacting portion in the form of a distendable membrane which is shaped to define a chamber, the membrane being formed from an elastomeric material and the chamber having a thin walled externally convex end region which is arranged in use of the mask to be depressed by and to accommodate the nose of a wearer.

(b) a gas supply port communicating with the chamber and connectable to a supply of pressurised gas which, when admitted to the chamber, causes the membrane to distend outwardly, (c) retaining means for holding the face contacting portion in contact with the face of the wearer whereby the end region of the chamber is caused to overlay at least the nose portion of the wearer's face and, under the influence of the pressurized gas, to conform with the contours of the overlayed region, and (d) at least one orifice formed within the membrane, the orifice being shaped and positioned to admit gas from the chamber to the nasal passages of the wearer.

The face contacting portion of the mask according to the present invention may be considered as having a shape which is unrelated to that of the intended wearer until such time as the mask is charged with gas and fitted to the wearer. However, when so charged and fitted, the membrane is caused to distend, to overlay the covered facial regions and to conform three-dimensionally with the facial contours of the wearer. In so doing, the membrane is caused to deform locally to accommodate individual facial projections and depressions, and distortions of the type that might otherwise create peripheral air leakage passages are thereby avoided. This is to be contrasted with the prior art masks which are moulded or are otherwise constructed with a clearly defined perimeter shape which is intended to match that of an intended wearer and which, except in the event of a perfect fit, must be distorted to match the features of the wearer.

Thus, the mask in accordance with the present invention may be viewed as a self-conforming mask which, by overlaying and conforming to the shape of the wearer provides an inherently large self-sealing area.

PREFERRED FEATURES OF THE INVENTION

The gas supply port and the retaining means may be secured to or be formed integrally with the distendable membrane itself. However, the distendable membrane is preferably mounted to a shell which is shaped to overfit the nose region at least of the wearer and which cooperates with the membrane to define the chamber. When this preferred arrangement is employed the retaining means would normally be connected to the shell and the gas supply port would normally be provided in a wall of the shell.

The shell is preferably moulded from a rigid plastics material and the membrane, which normally would be moulded from an elastic plastics material, is preferably removably mounted to a peripheral portion of the shell.

The distendable membrane is preferably secured to or moulded as an extension of a connector moulding which is arranged to mount the membrane to the shell. The connector moulding may be configured to contact facial regions of the wearer and, thus, be employed to locate the mask in a desired position on the face of the wearer. However, it is intended that the connector moulding should not interfere in any way with the face conforming feature of the distendable membrane.

When the membrane is formed with a single orifice, such orifice may be formed as an aperture which is shaped and sized to permit unimpeded communication between the chamber and the nasal passages of a wearer to whom the mask is fitted. Alternatively, the aperture may be shaped and sized to permit communication between the chamber and the nares-mouth region of the wearer, so that the mask may be employed as a full face mask. As a further alternative, two apertures may be provided for aligning with the respective nasal passages. However, when the membrane is formed with two orifices they preferably will be provided within respective nipples which are shaped and positioned to project into the nasal passages of the wearer to whom the mask is fitted. The nipples are preferably moulded integrally with the remaining portion of the membrane, so that they may be positioned and shaped elastically to match the wearer.

The invention will be more fully understood from the following description of two embodiments of a nasal mask which is suitable for use in administering air to persons who suffer from sleep apnea. The description is provided with reference to the accompanying drawings.

BRIEF DESCRIPTION OF THE DRAWINGS

In the drawings

FIG. 4 shows a rear elevation view of the mask as illustrated in FIG. 2 and as seen in the direction of arrow 4 shown in FIG. 2, FIG. 5 shows a sectional elevation view of a portion of the mask as seen in the direction of section plane 5—5 shown in FIG. 3.

DETAILED DESCRIPTION OF THE INVENTION

Figure 1:
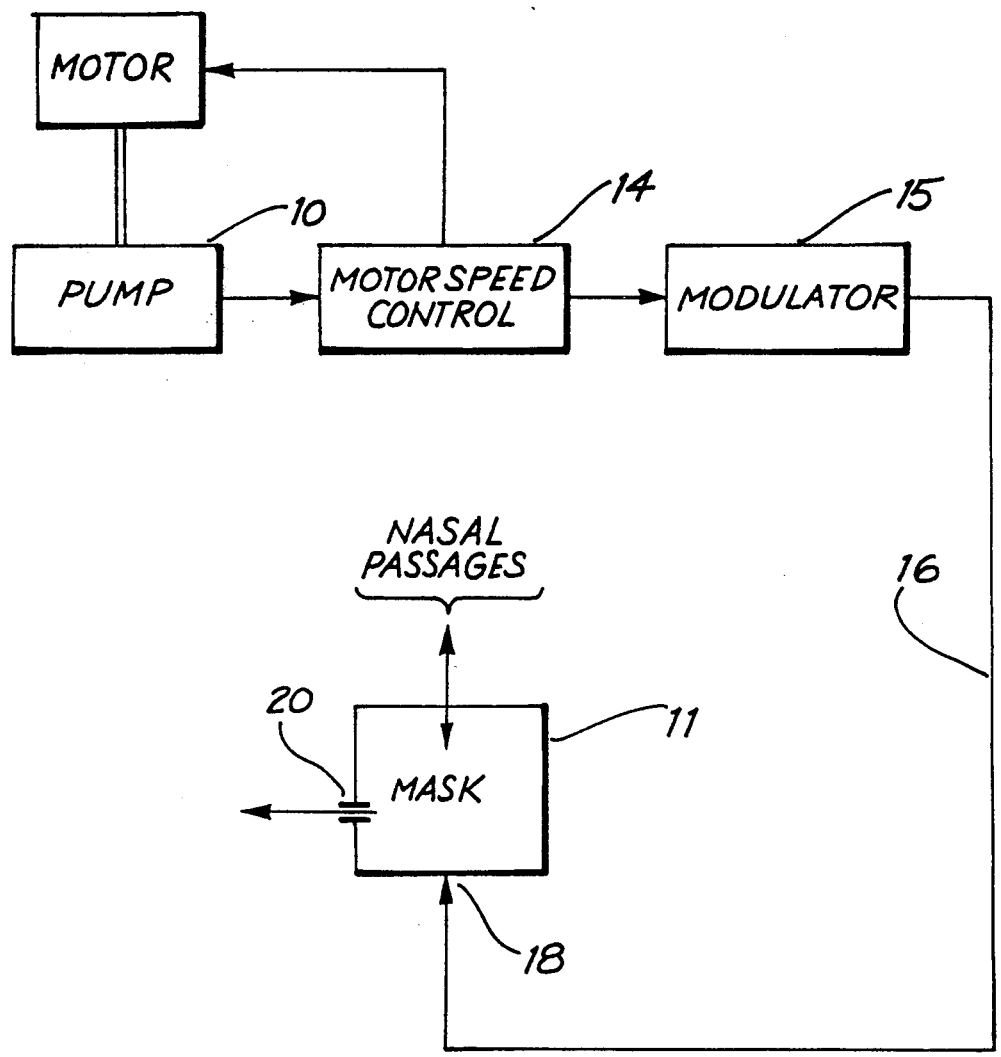
FIG. 1 shows a schematic illustration of a continuous positive airway pressure (CPAP) circuit in which the mask may be used.
Figure 2:
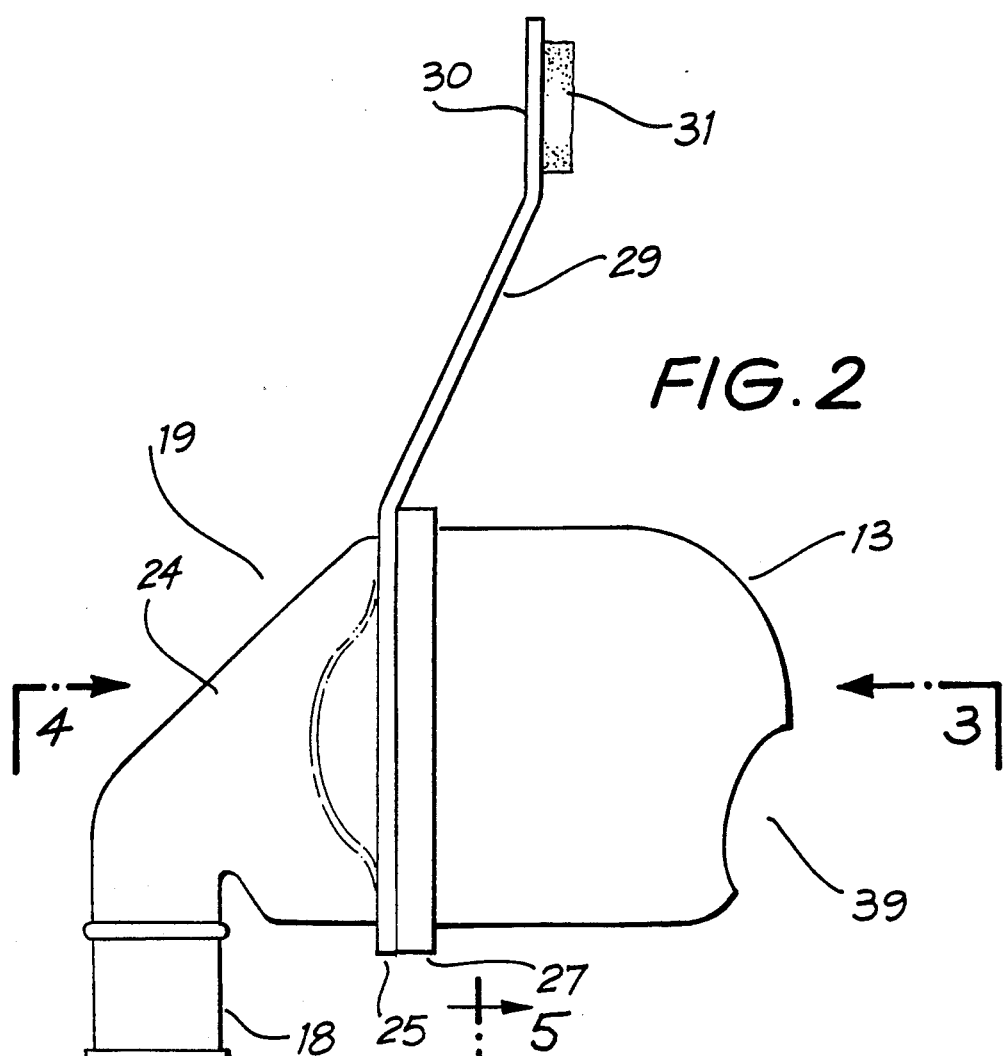
FIG. 2 shows a side elevation view of one embodiment of the mask.
Figure 3:
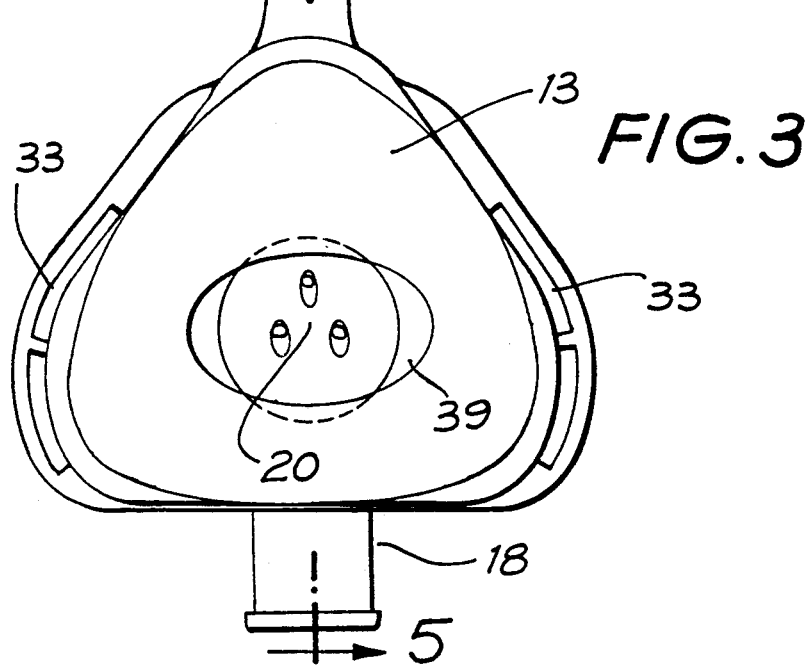
FIG. 3 shows a front elevation view of the mask as illustrated in FIG. 2 and as seen in the direction of arrow 3 shown in FIG. 2.

As illustrated in FIG. 1, the CPAP circuit comprises a motor driven pump 10 which is arranged to provide an air supply to a mask 11 which is fitted to a wearer 12 in the manner shown in FIG. 8. The air is supplied at a flow rate greater than the rate at which the air would normally be inspired in order to create backpressure within the circuit, whilst the wearer maintains regular breathing, in order that a membrane portion 13 of the mask will be caused to distend in the manner which is to be described in greater detail below. A motor speed controller 14 is located in circuit with the pump 10 and functions effectively to control the air pressure in the system to meet the requirements of individual persons. Also, a modulator 15 may optionally be located in circuit with the pump for modulating the pressure at which the air is delivered to the mask. The modulator is arranged, to provide pressure modulation within the range of 5% to 50% and at a frequency in the range 5 Hz to 60 Hz in order to effect stimulation of respiratory tract muscles in the wearer 12.

The air is conveyed to the mask 11 by way of a delivery line 16 and a supply port 18 in a shell portion 19 of the mask.

As illustrated, the mask is in general shaped to cover the nose area of the person 12 to whom the air is to be supplied and does not cover the mouth of the person. Thus, air from the supply port 18 is directed into the upper air passage of the person by way of the mask 11 and the person's nasal passages. However, it will be understood that the primary feature of the mask, namely the distendable membrane 13 may be incorporated in a full face mask, in which case the mask will be shaped to cover both the nose and mouth of the person.

Excess air, that is air which is not inspired during normal breathing, is vented to the atmosphere by way of a multi-aperture orifice 20 in the shell portion 19 of the mask 11. The orifice 20 presents a resistance to the air flow, so that a continuous positive pressure is maintained within the circuit and, thus, within the mask. By maintaining this pressure, the air which is breathed by the person 12 to whom the mask is fitted causes a pressure to be maintained in the upper airway of the person during normal inspiration and expiration.

Air which is expired by the person 12 is also vented to atmosphere by way of the orifice 20.

The shell 19 of the mask is moulded from a rigid plastics material and it has a body portion 24 around which a flange 25 extends. As can best be seen from FIG. 5, a lip 26 projects forwardly of the body portion 24 and a connector moulding 27, which carries the distendable membrane portion 13, overfits the lip 26. The interior of the shell 19 forms a cavity 28 which is defined in part by the membrane 13 and the connector moulding 27, and air is admitted to the cavity 28 from the support port 18.

An arm 29 extends upwardly from the body portion 24 of the shell and is angled such that an upper head engaging portion 30 of the arm will contact the forehead of the person 12 to whom the mask is fitted. A pad 31 of cushioning material is adhered to the head engaging portion 30 and slots 32 are located in that portion to accommodate harness straps 42 which are used to secure the mask to the head of the person 12. Additional slots 33 are formed within the peripheral flange 25 of the shell body portion 24 for receiving further harness straps 43.

The connector moulding 27 has a peripheral flange 34 in which a circumferential recess 35 is located. The recess 35 is positioned to overfit the shell lip 26 and the recess serves to hold the moulding 27 captive to the shell 19. The moulding 27 might be configured to provide an elementary support for the membrane 13 or, in an alternative arrangement, the membrane might be formed integrally with the moulding 27. However, as illustrated, the moulding 27 is formed separately from the membrane 13 and includes an integral wall 36 which is profiled at region 37 to locate around the nasal bridge of the wearer 12 and at region 38 to fit against the upper lip of the wearer.

The membrane 13 is formed as a thin-walled balloon-like pocket, and is moulded from a soft, flexible plastics material. The membrane is adhered to the wall 36 of the moulding 27, and an aperture 39 is formed within the membrane 13. The aperture 39 is shaped, positioned and sized to provide air passage communication between the chamber 28 of the mask and the nasal passages of the wearer 12, and various size membranes 13 may be provided to accommodate different size wearers, for example adults and children.

A small orifice (not shown in the drawings, may be provided in the membrane to act as a vent for any moisture that might otherwise build up between the mask and the wearer's face.

Figure 6:
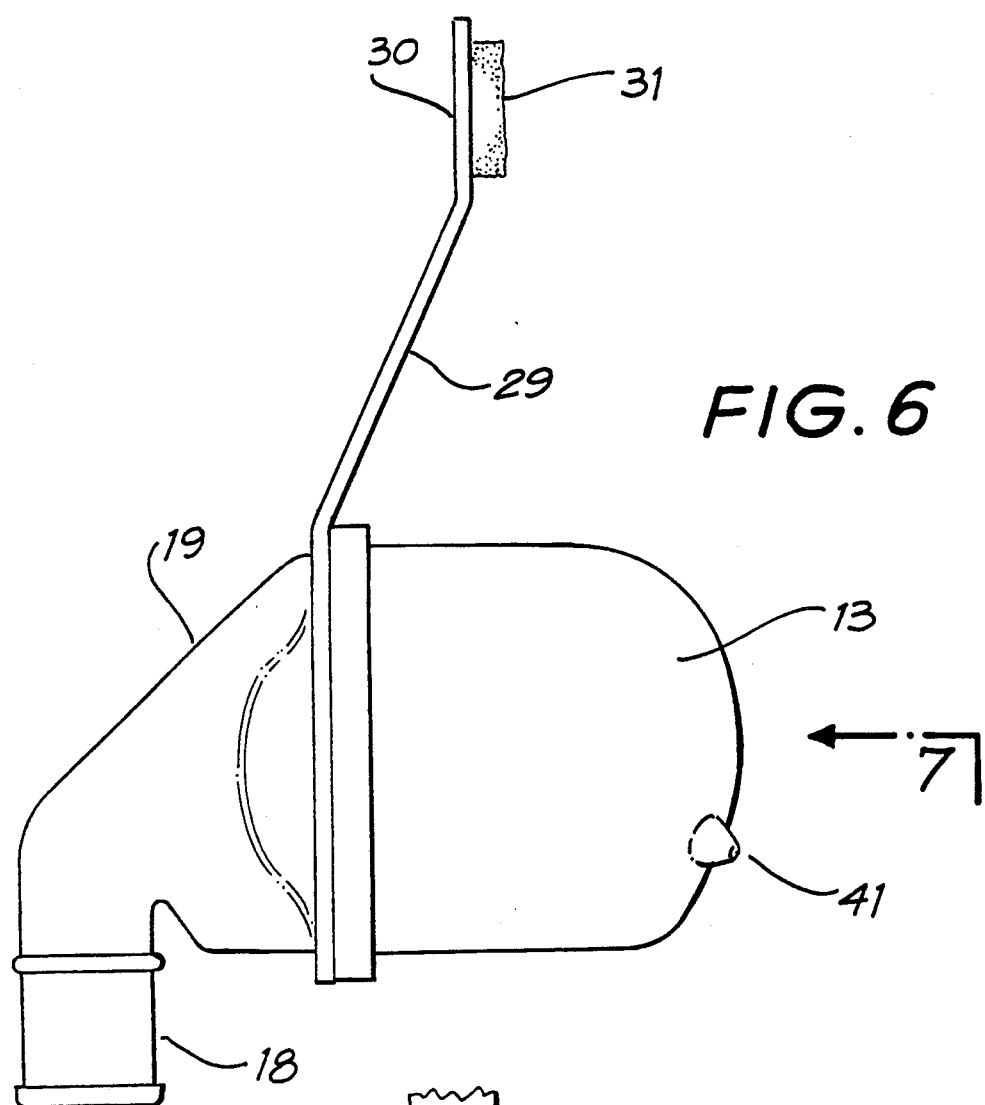
FIG. 6 shows a side elevation of a second embodiment of the mask.
Figure 7:
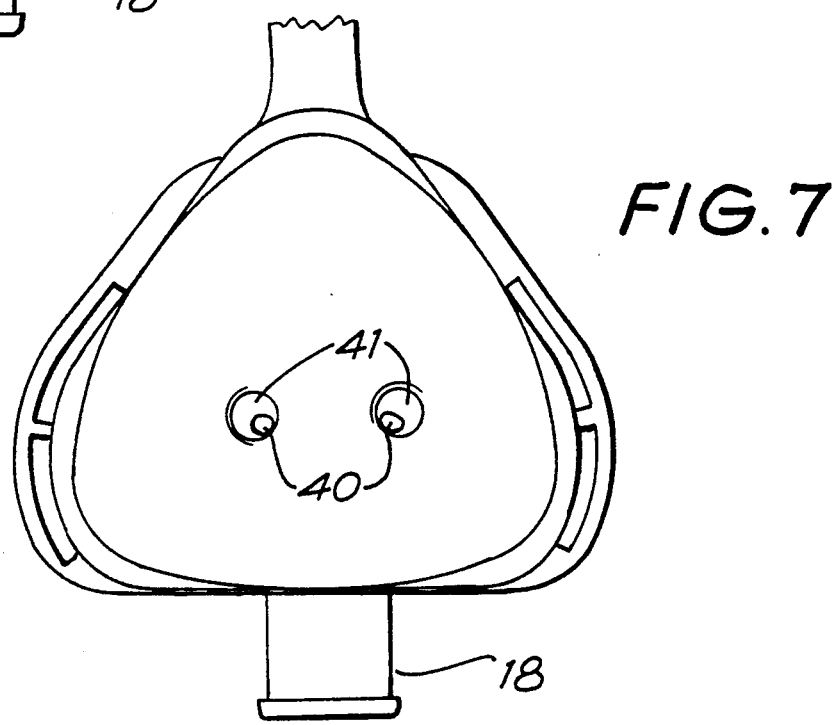
FIG. 7 shows a front elevation view of the mask as illustrated in FIG. 6 and as seen in the direction of arrow 7 as shown in FIG. 6, and FIGS. 8A, B and C illustrate sequentially the fitting of the mask as illustrated in FIGS. 1-5 to a wearer.

In the alternative arrangement shown in FIGS. 6 and 7, the air passage between the chamber 18 of the mask and the nasal passages of the wearer is provided by way of two orifices 40 which are located within respective nipples 41. The nipples themselves are shaped, positioned and sized to fit within the nasal passages of the wearer 12.

Figure 8A:
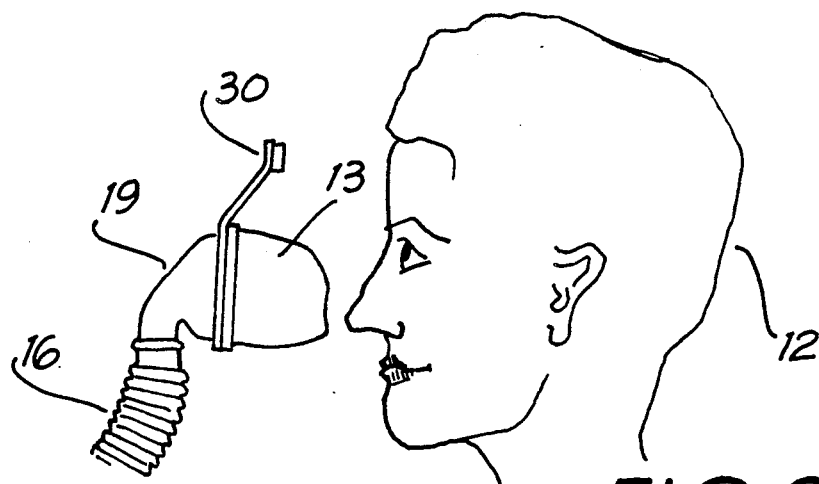
Figure 8B:
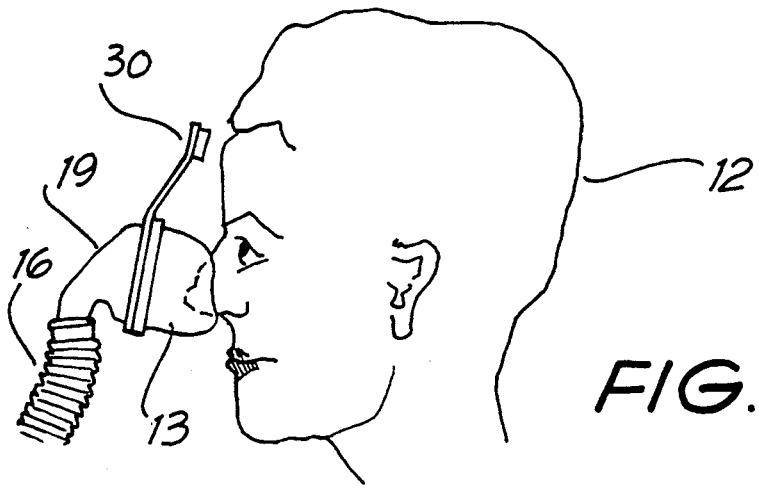
Figure 8C:
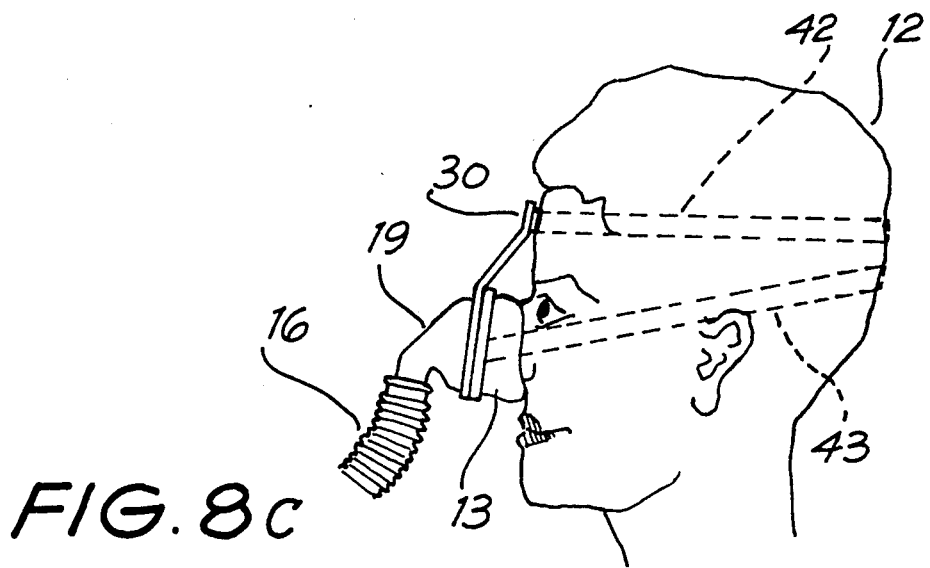

As shown in the sequential illustrations of FIGS. 8A to 8C, when fitting the nasal mask to the wearer 12, the mask is first connected to the pressurised air supply so that the membrane 13 is caused to billow or distend outwardly from the shell 19. A face contacting portion of the mask is then placed in contact with the wearer's nose and is positioned such that the aperture 39 or the nipples 41 align with the nasal passages. In this condition, as shown in FIG. 8B of the drawings, the membrane 13 will begin moulding around the nose of the wearer.

As the mask is pushed further into position, the shell 19 is moved closer to the wearer's nose and, under the influence of the air pressure within the chamber 28, the membrane 13 moulds completely around the nose of the wearer and conforms to the facial contours which are actually overlayed by the membrane. The mask is then pushed into its final position, as indicated in FIG. 8C and the retaining harness, indicated by the chain dotted lines 42 and 43, is positioned around the wearer's head to retain the mask in position.

We claim:

1. A nasal mask which comprises a face contacting portion in the form of a membrane which is shaped to define an inflatable chamber, the membrane being formed from an elastomeric material and the chamber having a thin, externally convex end region which is arranged in use of the mask to be depressed by and to accommodate the nose of a wearer, a gas supply port communicating with the chamber and connectable to a supply of pressurized gas which, when admitted to the chamber, causes the membrane to balloon outwardly, retaining means for holding the face contacting portion in contact with the face of the wearer, the ballooned end region of the chamber overlies at least a nose region of the wearer's face, and, under the influence of the pressurized gas, moulds, and seals three dimensionally and completely around the nose of the wearer and conforms with the contours of the overlayed region of the wearer's face and at least one orifice formed within the membrane, the orifice being shaped and positioned to admit gas from the chamber to the nasal passages of the wearer.

2. A nasal mask as claimed in claim 1, wherein the membrane is removably mounted to a shell, wherein the shell defines a cavity in fluid communication with the chamber formed by the membrane and wherein the gas supply port is formed as a part of the shell.

3. A nasal mask as claimed in claim 1 wherein one only said orifice is formed within the membrane, the orifice being in the form of an aperture which is shaped and sized to permit communication between the chamber and both nasal passages of the wearer.

4. A nasal mask as claimed in claim 1 wherein one only said orifice is formed within the membrane, the orifice being in the form of an aperture which is shaped and sized to provide communication between the chamber and both the nasal passages and the mouth of the wearer.

5. A nasal mask as claimed in claim 1 wherein two said orifices are formed within the membrane, the orifices being provided within respective nipples which are shaped and positioned to project into the nasal passages of the wearer when the mask is fitted to the wearer.

6. A nasal mask which comprises a shell which is shaped to overfit at least a nose region of the face of a wearer and which defines a cavity, a face contacting portion in the form of a membrane which is mounted to the shell and which is shaped to define an inflatable chamber in fluid communication with said cavity in the shell, the membrane being formed from an elastomeric material and the chamber having a thin externally convex end region which is arranged in use of the mask to be depressed by and to accommodate the nose of the wearer, a gas supply port in the shell and communicating with the chamber by way of the cavity in the shell, the port be connectable to a supply of pressurized gas which, when admitted to the chamber, causes the membrane to balloon outwardly from the shell, retaining means for holding the face contacting portion in contact with the face of the wearer, the ballooned end region of the chamber overlies at least the nose region and, under the influence of the pressurized gas moulds, and seals three dimensionally and completely around the nose of the wearer and conforms with the contours of the overlayed region of the wearer's face, and at least one orifice formed within the membrane, the orifice being shaped and positioned to admit gas from the chamber to the nasal passages of the wearer.

7. A nasal mask as claimed in claim 6 wherein the shell is moulded from a rigid plastics material.

8. A nasal mask as claimed in claim 6 wherein the membrane is removably mounted to the shell.

9. A nasal mask as claimed in claim 8 wherein the membrane is mounted to the shell by way of a connector moulding.

10. A nasal mask as claimed in claim 9 wherein the membrane is formed integrally with the connector moulding.

11. A nasal mask as claimed in claim 10 wherein the end region of the chamber extends outwardly from a relatively thick wall region, the wall region being configured to conform with the facial regions of the wearer.

12. A nasal mask as claimed in claim 9 wherein the membrane is formed separately from and is adhered to the connector moulding 13. A nasal mask as claimed in claim 12 wherein the connector moulding is located predominantly within the membrane and is configured to conform with facial regions of the wearer.

14. A nasal mask as claimed in claim 6, wherein only one orifice is formed within the membrane, the orifice being in the form of an aperture which is shaped and sized to permit communication between the chamber and both nasal passages of the wearer.

15. A nasal mask as claimed in claim 6, wherein only one orifice is formed within the membrane, the orifice being in the form of an aperture which is shaped and sized to provide communication between the chamber and both the nasal passages and the mouth of the wearer.

16. A nasal mask as claimed in claim 6, wherein two orifices are formed within the distendable membrane, the orifices being provided within respective nipples which are shaped and positioned to project into the nasal passages of the wearer when the mask is fitted to the wearer.

17. A continuous positive airway pressure (CPAP) system which comprises a motor driven pump, means for controlling the speed of the motor and a nasal mask connected in circuit with the pump, the nasal mask comprising a face contacting portion in the form of a membrane which is shaped to define an inflatable chamber, the membrane being formed from an elastomeric material and the chamber having a thin externally convex end region which is arranged in use of the mask to be depressed by and to accommodate the nose of a wearer, a gas supply port communicating with the chamber and connected to a supply of pressurized gas which, when admitted to the chamber causes the membrane to balloon outwardly, retaining means for holding the face contacting portion in contact with the face of the wearer, the ballooned end region of the chamber overlies at least a nose region of the wearer's face and, under the influence of the pressurized gas, moulds, and seals three dimensionally and completely around the nose of the wearer and conforms with the contours of the overlayed region of the wearer's face, and at least one orifice formed within the membrane, the orifice being shaped and positioned to admit gas from the chamber to the nasal passages of the wearer.

18. A continuous positive airway pressure (CPAP) system which comprises a motor driven pump, means for controlling the speed of the motor and a nasal mask connected in circuit with the pump, the nasal mask comprising a shell which is shaped to overfit at least a nose region of the face of a wearer and which defines a cavity, a face contacting portion in the form of a membrane which is mounted to the shell, the membrane being shaped to define an inflatable chamber in fluid communication with said cavity in the shell, the membrane being formed from an elastomeric material and the chamber having a thin externally convex end region which is arranged in use of the mask to be depressed by and to accommodate the nose of the wearer, a gas supply port in the shell and communicating with the chamber by way of the cavity in the shell, the port being connected to a supply of pressurized gas which, when admitted to the chamber, causes the membrane to balloon outwardly from the shell, retaining means for holding the face contacting portion in contact with the face of the wearer, the ballooned end region of the chamber overlies the nose region and, under the influence of the pressurized gas, moulds, and seals three dimensionally and completely around the nose of the wearer and conforms with the contours of the overlayed region of the wearer's face, and at least one orifice formed within the membrane, the orifice being shaped and positioned to admit gas from the chamber to the nasal passages of the wearer.

19. A nasal mask which comprises a shell shaped to overfit at least a nose region of a face of a wearer, said shell defining a first chamber;

a face contacting portion in the form of a distendable, inflatable membrane mounted to the shell, the membrane shaped to define a second chamber in fluid communication with said first chamber, said membrane formed from an elastomeric material, said second chamber having a thin-walled externally convex end region, said membrane depressed by and accommodating the nose of the wearer in use of said mask;

a gas supply portion in said shell communicating with said first chamber, said port connected to a supply of pressurized gas, said membrane distended outwardly from said shell upon admission of the gas into said first and second chambers;

retaining means for holding said face contacting portion in contact with the face of the wearer, said end region of said second chamber overlaying the nose region of the face of the wearer, said end region conforming to the contours of the overlayed portions of the face of the wearer under the influence of the pressured gas;

two nipples formed within said distendable, inflatable membrane, said nipples shaped and positioned to project into the nasal passages of the wearer when said mask is fitted on the face of the wearer, and two orifices formed within the distendable, inflatable membrane, one of said two orifices provided within each of said two nipples.

* * * * *

UNITED STATES PATENT AND TRADEMARK OFFICE
CERTIFICATE OF CORRECTION

PATENT NO. : 5,243,971
DATED : Sept. 14, 1993
INVENTOR(S) : Colin E. Sullivan et al Page 1 of 2

It is certified that error appears in the above-indentified patent and that said Letters Patent is hereby corrected as shown below:

On title page,

Item [57] lines 9 and 14
 delete "pressurised" and substitute therefor
 --pressurized--

On column 2, line 15, please delete "pressurised" and substitute therefor --pressurized--

On column 5, line 24, please delete "pressurised" and substitute therefor --pressurized--

On column 1, line 18, please delete "anaesthesic" and substitute therefor --anesthetic--

On column 1, line 37, please delete "localised" and substitute therefor --localized--

Column 3, line 63, delete "whilst" and
 substitute therefor --while--

UNITED STATES PATENT AND TRADEMARK OFFICE
CERTIFICATE OF CORRECTION

PATENT NO. : 5,243,971
DATED : September 14, 1993
INVENTOR(S) : Colin E. Sullivan et al It is certified that error appears in the above-indentified patent and that said Letters Patent is hereby corrected as shown below:

On column 3, line 67, please delete "lo" and substitute therefor --10--

On column 4, line 5, please delete "," after the word "arranged"

On column 6, lines 3 and 4, please delete "one only said" and substitute therefor --only one--

Signed and Sealed this

Fourteenth Day of June, 1994

Attest:

BRUCE LEHMAN

*Attesting Officer*    Commissioner of Patents and Trademarks